United States Patent
Filion et al.

(10) Patent No.: US 7,125,858 B2
(45) Date of Patent: Oct. 24, 2006

(54) HYALURONIC ACID IN THE TREATMENT OF CANCER

(75) Inventors: Mario C. Filion, Laval (CA); Nigel C. Phillips, Pointe-Claire (CA)

(73) Assignee: Bioniche Life Sciences Inc., Belleville (CA)

(*) Notice: Subject to any disclaimer, the term of this patent is extended or adjusted under 35 U.S.C. 154(b) by 0 days.

(21) Appl. No.: 10/168,327

(22) PCT Filed: Dec. 28, 2000

(86) PCT No.: PCT/CA00/01562

§ 371 (c)(1),
(2), (4) Date: Aug. 29, 2002

(87) PCT Pub. No.: WO01/47561

PCT Pub. Date: Jul. 5, 2001

(65) Prior Publication Data

US 2003/0176381 A1    Sep. 18, 2003

Related U.S. Application Data

(60) Provisional application No. 60/173,375, filed on Dec. 28, 1999.

(51) Int. Cl.
| | |
|---|---|
| A61K 31/70 | (2006.01) |
| A61K 31/00 | (2006.01) |
| A61K 38/00 | (2006.01) |
| C12N 1/00 | (2006.01) |
| C12N 1/20 | (2006.01) |
| A01N 63/00 | (2006.01) |
| C07H 21/02 | (2006.01) |

(52) U.S. Cl. ............... 514/44; 514/1; 514/2; 435/243; 435/253.1; 424/93.1; 536/23.1

(58) Field of Classification Search ............... 435/691, 435/320.1, 325, 455; 514/2, 44, 54
See application file for complete search history.

(56) References Cited

U.S. PATENT DOCUMENTS

| | | |
|---|---|---|
| 3,172,815 A | 3/1965 | Fox et al. |
| 3,976,544 A | 8/1976 | Adam et al. |
| 4,010,257 A | 3/1977 | Adlam et al. |
| 4,036,953 A | 7/1977 | Adam et al. |
| 4,152,423 A | 5/1979 | Adam et al. |
| 4,182,751 A | 1/1980 | Ayme |
| 4,337,243 A | 6/1982 | Ayme |
| 4,520,019 A | 5/1985 | Ribi et al. |
| 4,579,941 A | 4/1986 | Furutani et al. |
| 4,647,456 A | 3/1987 | Pulverer |
| 4,663,306 A | 5/1987 | Cantrell |
| 4,724,144 A | 2/1988 | Rook et al. |
| 4,726,947 A | 2/1988 | Shimada et al. |
| 4,744,984 A | 5/1988 | Ragland |
| 4,877,611 A | 10/1989 | Cantrell |
| 5,759,554 A * | 6/1998 | Alkemade et al. ........ 424/282.1 |
| 5,827,834 A * | 10/1998 | Falk et al. .................... 514/54 |
| 5,888,986 A | 3/1999 | Morales et al. |
| 6,326,357 B1 | 12/2001 | Phillips et al. |
| 6,329,347 B1 | 12/2001 | Phillips et al. |
| 6,475,795 B1 * | 11/2002 | Turley et al. ............... 435/455 |

FOREIGN PATENT DOCUMENTS

| | | |
|---|---|---|
| EP | 0 158 075 A1 | 2/1985 |
| EP | 0 308 197 A2 | 9/1988 |
| EP | 0 343 480 A1 | 5/1989 |
| WO | WO 87/02679 | 5/1987 |
| WO | WO 94/16727 | 8/1994 |
| WO | WO 94 20115 A | 9/1994 |
| WO | WO 95 30423 | 11/1995 |
| WO | WO 97/33612 | 9/1997 |
| WO | WO 98 17320 | 4/1998 |
| WO | WO/9817320 * | 4/1998 |
| WO | WO 99 02151 A | 1/1999 |
| WO | WO 99/07383 | 2/1999 |
| WO | WO 99/42113 | 8/1999 |
| WO | WO 00/33875 | 6/2000 |
| WO | WO 00 41730 A | 7/2000 |
| WO | WO 00/56269 A2 | 9/2000 |

OTHER PUBLICATIONS

Hode-Dufour et al J. Immunology 159:2492-2500, 1997.*
Vincent et al J. Biol.Chem. 276(18):14728-14736, 2001.*
Gomez-Navarro et al, Eur. J. Cancer. 35(6);867-885, 1999.*
Freemantle, C., et al., "The Modulation of Granulomatous Tissue and Tumour Angiogenesis by Diclofenac in Combination with Hyaluronan (Hyal Ex-0001)," *Int. J. Tiss. Reac.*, vol. XVII (4), pp. 157-166 (1995).
V. Assmann, et al., "The Human Hyaluronan Receptor RHAMM is Expressed as an Intracellular Protein in Breast Cancer Cells," Journal of Cell Science 111, pp. 1685-1694 (1998).
H. Brem, M.D., et al., "Interstitial Chemotherapy with Drug Polymer Implants for the Treatment of Recurrent Gliomas," *J. Neurosurg*, vol. 74, pp. 441-446 (Mar. 1991).
G. P. Dimri, et al., "A biomarker that Identifies Senescent Human Cells in Culture and in Aging Skin *In Vivo*," Proc. Natl. Acad. Sci. USA, vol. 92, pp. 9363-9367 (Sep. 1995).

(Continued)

Primary Examiner—Sumesh Kaushal
(74) Attorney, Agent, or Firm—Kilpatrick Stockton LLP

(57) ABSTRACT

The present invention relates to a composition and method comprising purified HA, a second anti-neoplastic agent and a pharmaceutically acceptable carrier, wherein the purified HA and the second anti-neoplastic agent are administered to a mammal having cancer in an amount effective to treat the cancer.

19 Claims, No Drawings

OTHER PUBLICATIONS

Eck et al., "Goodman & Gilman's The Pharmacological Basis of Therapeutics," Chap. 5: Gene-Based Therapy, McGraw-Hill, New York, p. 77-101, dated 1996.

Filion, M.C. et al., "Mycobacterial Cell Wall—DNA Complex Induces Apoptosis in Cancer Cells," *J. Pharm. Pharmacol.*, vol. 50 (Supplement), p. 39 (1998).

Filion, M.C. et al., "Mycobacterial Cell Wall-DNA Complex (MCC) Induces Cell Cycle Arrest at the Late S+G$_2$M Phase in Leukemic Cells," British Journal Of Cancer, GB, London, vol. 80, No. Suppl. 02, Jul. 1999, p. 76, XP000892420 (Abstract).

Filion M. C., et al., "Mycobacterial DNA Induces Apoptosis in Myeloid Leukemia Cell Lines," 39th Ann. Mtg. Amer. Soc. Herm., Dec. 1997 (Abstract).

Filion M.C., et al.; "*Mycobacterium phlei* Cell Wall Complex, a New Anti-Tumoral Agent, Induces IL-12 Synthesis by Monocyte-Macrophages via Associated DNA," 39th Ann. Mtg. Amer. Soc. Herm. Dec. 1997.-*

Filion, M.C., et al., "*Mycobacterium phlei* Cell Wall Complex, a New Anti-Tumoral Agent, Induces IL-12 Synthesis by Monocyte/Macrophages via Associated DNA," Blood, Nov. 15, 1997, p. 58b (2859), vol. 90, No. 10, Suppl. 1. (Abstract).

Filion, M.C. et al., "*Mycobacterium phlei* Cell Wall Complex Directly Induces Apoptosis in Human Bladder Cancer Cells,"*British J. of Cancer*, vol. 79, No. 2, pp. 229-235 (1999).

Filion, et al., "Toxicity and Immunomodulatory Activity of Liposomal Vectors Formulated with Cationic Lipids Toward Immune Effector Cells," Biochim Biophys Acta, 1997, 345-356, vol. 1329.

Gray, G.R., et al., "Brief Communication: Immunotherapy of Cancer: Tumor Suppression and Regression by Cell Walls of *Mycobacterium phlei* Attached to Oil Droplets," *J. Natl. Cancer Instit.*, vol. 55, No. 3, pp. 727-730 (Sep. 1975)

Kataoka T., et al., "Antitumor Activity of Synthetic Oligonucleotides with Sequences from cDNA Encoding Proteins of *Mycobacterium-Bovis* BCG", *JPN J. Can. Res.*, vol. 83, No. 3, pp. 244-247, 1992.

Kishore et al., "Induction of Cell Mediated Immune Response by Nonspecific Stimulator of Immunity Against Antigenically Unrelated Oncogenic Virus," (Marek's disease virus) Indian Journal or Experimental Biology, vol. 27: 529-531 (Jun. 1989).

Klinman, D.M. et al., "CpG Motifs Present in Bacterial DNA Rapidly Induce Lymphocytes to Secrete Interleukin 6, Internleukin 12, and Interferon γ," *Proc. Natl. Acad. Sci. USA*, vol. 93, pp. 2879-2883 (Apr. 1996).

Mallick et al., "Nonspecific Immunostimulation Against Viruses," Comp. Immun. Microbiol. Infect. Dis. vol. 8(1):53-63 (1985).

Mashiba H., et al., "In-vitro Augmentation of Macrophage-Activating-Factor Release from Peripheral Blood Cells of Cancer Patients by a DNA Fraction from *Mycobacterium bovis* BCG," Japanese Journal of Medical Science and Biology, Aug. 1990, 43 (4) 133-9, Journal Code: KLZ. ISSN: 0021-5112, XP002085536.

E. Marshal, Science vol. 269, p. 1052-1053 (Aug. 1995).

C. M. McKee, et al., "Hyaluronan Fragments Induce Nitric-oxide Synthase in Murine Macrophages through a Nuclear Factor KB-dependent Mechanism," JBC Online, The American Society for Biochemistry and Molecular Biology, Inc., vol. 272, No. 12, pp. 8013-8018 (Mar. 21, 1997).

C. M. McKee, et al., "Hyaluronan (HA) Fragments Induce Chemokine Gene Expression in Alveolar Macrophages," J. Clin. Invest., The American Society for Clinical Investigation, Inc., vol. 98, No. 10, pp. 2403-2413 (Nov. 1996).

Morales, A., et al., "Immunotherapy of an Experimental Adenocarcinoma of the Prostate," *J. of Urology*, vol;. 153, pp. 1706-1710 (May 1995).

Ossina et al., "Interferon-Gamma Modulates a P53-Independent Apoptotic Pathway and Apoptosis Related Gene Expression," J. Biol. Chem. vol. 272(26): 16351-16357 (Jun. 27, 1997).

Pisetsky, D.S., et al., "Immune Activation by Bacterial DNA: A New Genetic Code," *Immunity*, vol. 5, pp. 303-310, (Oct. 1996).

Pisetsky, D.S., et al., "Stimulation of *In Vitro* Proliferation of Murine Lymphocytes by Synthetic Oligodeoxynucleotides," *Mol. Biol. Reports*, vol. 18, pp. 217-221 (1993).

Phillips, et al., "Influence of Phospholipid Compositions on Antibody Responses to Liposome Encapsulated Protein and Peptide Antigens," Vaccine, pp. 898-904, vol. 14, No. 9 (1996).

Reader, S., et al., "Mycobacterial Cell Wall-DNA Complex (MCC) Inhibits Proliferation and Induces Apoptosis in Androgen-Dependent and Independent Human Prostate Cancer Cells," British Journal of Cancer, p. 190, vol. 80, No. 2 (Jul. 1999) (Abstract).

Rojas M., et al., "Differential Induction of Apoptosis by Virulent *Mycobacterium tuberculosis* in Resistant and Susceptible Murine Macrophages: Role of Nitric Oxide and Mycobacterial Products", *J. of Immun.*, vol. 159, No. 3, pp. 1352-1362, (Aug. 1997).

G. R. Screaton, et al., "Genomic Structure of DNA Encoding the Lymphocyte Homing Receptor CD44 Reveals at Least 12 Alternatively Spliced Exons", Proc. Natl. Acad. Sci. USA, vol. 89, pp. 12160-12164 (Dec. 1992).

Shimada S., et al., "Antitumor Activity of the DNA Fraction from *Mycobacterium bovis* BCG. II. Effects on Various Syngeneic Mouse Tumors"; *J. of Nat. Can. Inst.*, vol. 74, No. 3, pp. 681-688 (Mar. 1985).

Tokunaga, T. et al., "Synthetic Oligonucleotides with Particular Base Sequences from the cDNA Encoding Proteins of *Mycobacterium bovis* BCG Induce Interferons and Activate Natural Killer Cells," *Microbiol. Immunol.*, vol. 36, No. 1, pp. 55-66 (1992).

Varadhachary et al., "Differential Ability of T Cell Subsets to Undergo Activation-Induced Cell Death," *PNAS* (USA) vol. 94: 5778-5783 (May 1987).

Verma et al., "Gene Therapy—Promises, Problems and Prospects," Nature Vo. 389, p. 239-242 (Sep. 1997).

Emile E. Voest, et al., "Inhibition of Angiogenesis In Vivo by Interleukin 12," Journal of the National Cancer Institute, vol. 87, No. 8 (Apr. 19, 1995).

Yamamoto, S. et al., "In-Vitro Augmentation of Natural Killer Cell Activity and Production of Inerferon-Alpha Beta and Gamma with DNA Fraction from *Mycobacterium bovis* BCG"; *JPN J Cancer Res.*, vol. 79, No. 7, pp. 866-873, 1988.

Zychlinsky et al., "Perspectives Series: Host/Pathogen Interactions," J. Clin. Invest. vol. 100(3): 493-496 (Aug. 1997).

* cited by examiner

SEQUENCE LISTING

```
<160> NUMBER OF SEQ ID NOS: 2

<210> SEQ ID NO 1
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 1 gggtgg                                                              6

<210> SEQ ID NO 2
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 2
gtgtgtgtgt gtgtgtgtgt gtgtgtg                                      27
```

HYALURONIC ACID IN THE TREATMENT OF CANCER

PRIOR RELATED APPLICATIONS

The present application is a National Phase of PCT/CA00/01562, filed Dec. 28, 2000, which claims priority to U.S. Provisional Patent Application No. 60/173,375, filed Dec. 28, 1999, which is hereby incorporated by reference in its entirety.

FIELD OF THE INVENTION

The invention relates to hyaluronic acid and a second anti-neoplastic agent in the treatment of cancer

BACKGROUND OF THE INVENTION

Hyaluronic acid (hereinafter, "HA") is a glycosaminoglycan with repeating disaccharide units of D-glucuronic acid and N-acetyl-D-glucosamine that exists as a high molecular mass polymer ($10^6$ to $10^7$ Da) in its native form (Laurent et al. FASEB J. 6:2397, 1992). HA is a major non-structural component of connective tissue and is important for maintaining extracellular matrix architecture and for promoting cell motility, adhesion and proliferation (Entwistle, J. Cell Biochem. 61:569, 1996).

The effects of both low molecular mass HA ($\leq 5 \times 10^5$ Da) and high molecular mass HA ($>5 \times 10^5$ Da) on normal cells has been studied extensively (McKee et al. J. Biol. Chem. 272:8013, 1997; Hodge-Dufour et al. J. Immunol. 159:2492, 1997; Rooney et al. Int J Cancer 60:632, 1995). However, little is known about the effects of HA on malignant cells. In vitro, HA (>0.320 mg/ml) inhibited proliferation of B16F10 murine melanoma cells by 50 to 90%. In vivo, HA (1 mg/ml), administered over 7 days by an Alzet osmotic pump into the immediate vicinity of a B16F10 murine melanoma tumor, reduced tumor volume >85%. In vivo, HA (>750 mg/kg) administered with various other therapeutic agents over various periods of time, reduced or eliminated rectal, gastric, breast, prostate and endometrial cancers (PCT/CA/00283). In vivo, hyaluronan (HA) (7.5 mg/kg), administered with 2.5 mg/kg of the lipophilic, tubulin-stabilizin, chemotherapeutic drug paclitaxel (TAXOL®), decreased tumor mass of colon 26-cells seeded into BALB/c mice. It was proposed that the water-insoluble paclitaxel binds to hydrophobic patches on HA and that the binds to HA receptors on the surface of malignant cells and, thereby, delivers the paclitaxel directly to the malignant cells (PCT/CA98/00660) That is, HA functions as a delivery agent for the paclitaxel and the efficiency of this delivery depends on the expression of HA cell surface receptors such as CD44. However, as colon-26 cancer cells express high levels of HA receptors, HA alone significantly inhibits the growth of these cancer cells (Freemantle et al Int. J. Tissue React. 17:157, 1995).

Cancer is an aberrant net accumulation of atypical cells that results from an excess of cell proliferation, an insufficiency of cell death, or a combination of the two. Cell proliferation is characterized by replication of total cellular DNA and the division of one cell into two cells (Hochhauser D. Anti-Cancer Chemotherapy Agents 8:903, 1997). Cell death is affected by immune-mediators including, but not limited to, IL-6 and IL-13 that initiate cytolytic processes and that promote apoptosis, and by apoptosis inducers that directly initiate pathways leading to cell death (Muzio et al. Cell 85:817, 1996; Levine, A. Cell 88:323, 1997).

Current cancer treatments act by inhibiting proliferation of cancer cells or by inducing apoptosis in cancer cells. However, many of these treatments have proven to be less than adequate for clinical applications and, at standard dosages, are inefficient or toxic, have significant adverse side-effects, result in development of drug resistance or immunosensitization, are debilitating and compromise the quality of life of the patient. Moreover, the costs of these treatments are substantial, both to the individual patient and to society.

Therefore, there is a continuing need for novel cancer treatments that inhibit proliferation of cancer cells, induce apoptosis in cancer cells, are effective at dose regimens associated with minimal toxicity, and are cost effective.

SUMMARY OF THE INVENTION

The present invention fulfills these needs by providing a composition and method comprising purified HA, a second anti-neoplastic agent and a pharmaceutically acceptable carrier, wherein the HA and the second anti-neoplastic agent act synergistically to potentiate each other's effect on cancer cells.

HA is a nontoxic anti-neoplastic agent that acts synergistically with other anti-neoplastic agents including, but not limited to, a chemotherapeutic drug to inhibit proliferation and induce apoptosis in cancer cells. As the HA and the chemotherapeutic drug potentiate each other's effect on cancer cells, the standard dose of the chemotherapeutic drug can be reduced without compromising the therapeutic effectiveness of the cancer treatment. Moreover, as HA is inexpensive and as most chemotherapeutic drugs are expensive, the combined use of HA and a chemotherapeutic drug can reduce significantly the cost of cancer treatment. The increase in dose effectiveness, decrease in toxicity and decrease in cost address long felt unfulfilled needs in the medical arts and provide important benefits for mammals, including humans.

Accordingly, it is an object of the present invention is to provide a composition and method effective to treat cancer in a mammal, including a human.

Another object is to provide a composition and method that reduces the toxic side-effects of cancer treatments.

Another object is to provide a composition and method that reduces the cost of cancer treatments.

Another object is to provide a composition and method, wherein two or more anti-neoplastic agents act synergistically on cancer cells.

Another object is to provide a composition and method that inhibits proliferation of cancer cells Another object is to provide a composition and method that induces apoptosis in cancer cells.

Another object is to provide a composition and method that potentiates the effect of chemotherapeutic drugs on cancer cells.

Another object is to provide a composition and method that potentiates the effect of anti-neoplastic nucleic acids on cancer cells.

Another object is to provide a composition and method that potentiates the effect of anti-neoplastic bacterial DNAs on cancer cells.

Another object is to provide a composition and method that potentiates the effects of anti-neoplastic bacterial DNA-bacterial cell wall complexes on cancer cells.

Another object is to provide a composition and method that potentiates the effect of anti-neoplastic bacterial cell wall extracts on cancer cells.

Another object is to provide a composition and method that potentiates the effect of anti-neoplastic synthetic oligonucleotides on cancer cells.

Another object is to provide a composition and method that stimulates the production of cytokines by immune system cells.

Another object is to provide a composition and method that stimulates the production of IL-6 by immune system cells.

Another object is to provide a composition and method that stimulates the production of IL-12 by immune system cells.

These and other objects, features and advantages of the present invention will become apparent after a review of the following detailed description of the disclosed embodiment and the appended claims.

DETAILED DESCRIPTION OF THE INVENTON

The present invention provides a composition comprising purified HA, a second anti-neoplastic agent and a pharmaceutically acceptable carrier, wherein the HA and the second anti-neoplastic agent act synergistically to potentiate each other's effect on cancer cells. The present invention also provides a method, wherein a composition comprising purified HA, a second anti-neoplastic agent and a pharmaceutically acceptable carrier is administered to a mammal having cancer in an amount effective to treat the cancer.

As used herein, "hyaluronic acid (HA)" refers to hyaluronan, hyaluronate, subunits of HA that have been tested and found suitable for use in a mammal, including a human.

As used herein, "anti-neoplastic agent" refers to any agent that inhibits the growth or metastases of a cancer.

As used herein, "chemotherapeutic drug" refers to any drug approved by a regulatory agency of a country or a state government or listed in the U.S. Pharmacopoeia or other generally recognized pharmacopoeia to treat cancer in a mammal, including a human.

As used herein, "non-lipophilic" refers to a chemotherapeutic drug having greater than zero solubility in water.

As used herein, "standard dose" refers to the dose or dose range suggested in the U.S. Pharmacopoeia or other generally recognized pharmacopoeia to treat cancer in a mammal, including a human.

As used herein, "synergism" refers to the coordinated action of two or more agents on the growth or metastases of a cancer.

As used herein, "potentiates" refers to a degree of anti-cancer activity that is greater than additive.

As used herein "toxic" refers to the adverse side-effects of an anti-neoplastic agent as included in the U.S. Pharmacopoeia or other generally recognized pharmacopoeia.

HA is highly viscous, highly electronegative and highly hydrophilic. Various methods for the isolation, purification and fractionation of HA are known to those skilled in the art. In addition, molecular mass fractions of purified HA can be purchased from commercial sources including, but not limited to, Fluka Chemical Corporation (Ronkonkoma, N.Y., USA), Genzyme Corporation (Cambridge, Mass., USA), Lifecore Inc. (Chaska, Minn., USA), Hyal Pharmaceutical Corporation (Mississauga, Ontario, Canada) and Bioniche Life Sciences, Inc. (Belleville, Ontario, Canada).

Anti-neoplastic agents include, but are not limited to, chemotherapeutic drugs, biologicals, immunostimulants, cytokines, antigens, antibodies, nucleic acids, synthetic oligonucleotides, vaccines, aptamers nucleic acids, antisense nucleic acids, immunomodulators, telomerase inhibitors, caspase activators, apoptosis inducers, cyclin inhibitors, CDK inhibitors, stable triple helix forming agents, genetically engineered, biologically engineered and chemically synthesized agents, agents that target cell death molecules for activation or inactivation, and combinations thereof.

Chemotherapeutic drugs include, but are not limited to, DNA-alkylating agents, DNA-cross-linking agents, antibiotic derivatives, topoisomerase inhibitors, tubulin stabilizers, tubulin destabilizers, antimetabolites, nitrogen mustard derivatives, steroids, hormone antagonists, protein kinase inhibitors, HMG-CoA inhibitors, metaloproteinase inhibitors, angiogenesis inhibitors, CDK inhibitors, cyclin inhibitors, caspase inhibitors, RNA, antisense RNA, DNA, antisense DNA, bacterial extracts, bacterial DNA, bacterial DNA-bacterial cell wall complexes, synthetic oligonucleotides, molecular biologically modified viral and bacterial components, and combinations thereof.

Pharmaceutically acceptable carriers include liquid carriers, solid carriers, or both. Liquid carriers include, but are not limited to, water, saline, physiologically acceptable buffers, aqueous suspensions, oil emulsions, water in oil emulsions, water-in-oil-in-water emulsions, site-specific emulsions, long-residence emulsions, sticky-emulsions, microemulsions and nanoemulsions. Preferred aqueous carriers include, but are not limited to, water, saline and physiologically acceptable buffers. Preferred non-aqueous carriers include, but are not limited to, a mineral oil or a neutral oil including, but not limited to, a diglyceride, a triglyceride, a phospholipid, a lipid, an oil and mixtures thereof. Solid carriers are biological carriers, chemical carriers, or both and include, but are not limited to, particles, microparticles, nanoparticles, microspheres, nanospheres, minipumps, bacterial cell wall extracts, and biodegradable or non-biodegradable natural or synthetic polymers that allow for sustained release of the composition (Brem et al. J. Neurosurg. 74: 441, 1991).

Cancers include, but are not limited to, squamous cell carcinoma, fibrosarcoma, sarcoid carcinoma, melanoma, mammary cancer, lung cancer, colorectal cancer, renal cancer, osteosarcoma, cutaneous melanoma, basal cell carcinoma, pancreatic cancer, bladder cancer, brain cancer, ovarian cancer, prostate cancer, leukemia, lymphoma and metastases derived therefrom.

Preferably, the molecular mass of the HA used is between about $1 \times 10^3$ and $1 \times 10^7$ Da, more preferably between about $5 \times 10^4$ and $1 \times 10^6$ Da, and most preferably between about $1 \times 10^4$ and $8 \times 10^5$ Da. Preferably, the amount of HA administered per dose is from about 0.001 to 25 mg/kg, more preferably from about 0.01 to 15 mg/kg, and most preferably from about 0.1 to 10 mg/kg. The amount of anti-neoplastic agent administered per dose depends on the anti-neoplastic agent used and is preferably about 5 to 75% of the standard dose, more preferably from about 5 to 50% of the standard dose, and most preferably from about 5 to 10% of the standard dose.

Routes of administration include, but are not limited to, oral, topical, subcutaneous, transdermal, subdermal, intra-muscular, intra-peritoneal, intra-vesical, intra-articular, intra-arterial, intra-venous, intra-dermal, intra-cranial, intra-lesional, intra-tumoral, intra-ocular, intra-pulmonary, intra-spinal, placement within cavities of the body, nasal inhalation, pulmonary inhalation, impression into skin, electroporation, osmotic minipumps, and through a cannula to the site of interest.

Depending on the route of administration, the volume per dose is preferably about 0.001 to 100 ml per dose, more preferably about 0.01 to 50 ml per dose, and most preferably about 0.1 to 30 ml per dose. The dose can be administered in a single treatment or in multiple treatments on a schedule and over a period of time appropriate to the cancer being treated, the condition of the recipient, and the route of administration. Moreover, the HA can be administered before, at the same time as, or after administration of the anti-neoplastic agent as long as both are administered within a 24 hour time period.

In an example, 100 mg of <$1.5 \times 10^4$ Da HA+4 mg/kg of the antimetabolite fluorinated pyrimidine 5-fluorouracil (hereinafter, "5-FU"; standard dose 12 mg/kg) are administered intravenously to a mammal having cancer in a number of doses and over a period of time effective to treat the cancer. In another example, 100 mg of $5.0-7.5 \times 10^5$ Da HA+2 mg/kg of 5-FU are administered intratumorally to a mammal having a cancer in a number of doses and over a period of time effective to treat the tumor. In another example, 100 mg of $5.0-7.5 \times 10^5$ Da HA+1.2 mg/kg of 5-FU are administered intratumorally to a mammal having a cancer in a number of doses and over a period of time effective to treat the tumor. In another example, 100 mg of $1-3 \times 10^5$ Da HA+10 mg/m$^2$ of the alkylating agent cisplatin (PLATINOL®; hereinafter, "CIS"; standard dose 100 mg/m$^2$) is administered intravenously to a mammal having cancer in a number of doses and over a period of time effective to treat the cancer. In another example, 100 mg of $3-5 \times 10^5$ Da HA+36 mg/m$^2$ of the DNA cross-linker carboplatin (PARAPLATIN®; standard dose 360 mg/m$^2$) is administered intravenously to a mammal having a cancer in a number of doses and over a period of time effective to treat the cancer.

The amount of HA per dose, the particular second anti-neoplastic agent used, the amount of the second anti-neoplastic agent per dose, the dose schedule and the route of administration should be decided by the practitioner using methods known to those skilled in the art and will depend on the type of cancer, the severity of the cancer, the location of the cancer and other clinical factors such as the size, weight and physical condition of the recipient. In addition, in vitro assays may be employed to help identify optimal ranges for HA+anti-neoplastic agent administration.

The following examples will serve to further illustrate the present invention without, at the same time, however, constituting any limitation thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Cells

All cell lines were obtained from the American Type Culture Collection (ATCC, Rockville, Md., USA) and were cultured in the medium recommended by the ATCC.

Table 1 shows the cell lines, their origins and their properties.

TABLE 1

Cell lines

| CELL LINE | ORIGIN | PROPERTIES |
|---|---|---|
| MCF-7 | Human breast cancer | Caspase 3-negative; estrogen-dependent |
| PC-3 | Human prostate cancer | p53 mutated; androgen-independent (hormone refractory) |
| LNCaP | Human prostate cancer | TGF-beta 1 receptor-negative; androgen-dependent |
| Du-145 | Human prostate cancer | Fas-resistant; Rb-mutated; p53 mutated; androgen independent |
| T-24 | Human bladder cancer | p53 mutated |
| RT-4 | Human bladder cancer | N.D. |
| UMUC-3 | Human bladder cancer | P-glycoprotein over-expression |
| HT-1376 | Human bladder cancer | p53 and p21 (waf-1) mutated |
| HT-1080 | Human fibrosarcoma | N.D. |
| B-16F1 | Murine melanoma | N.D. |

EXAMPLE 2

Reagents

HA, purified from *Streptococcus* sp., was obtained from Lifecore Inc. (Chaska, Minn., USA) and was dissolved in sterile saline at 0.8 mg/ml (CYSTISTAT®, Bioniche Life Sciences Inc., Belleville, Ontario, Canada) or at 10.0 mg/ml (SUPLASYN®, Bioniche Life Sciences Inc., Beliville, Ontario, Canada).

*Mycobacterium phlei*-DNA (hereinafter, "M-DNA") and M-DNA-*Mycobacterium phlei* cell wall complex (hereinafter, "MCC") were prepared as in U.S. application Ser. No. 09/129,312 (incorporated by reference herein).

EXAMPLE 3

Preparation of HA of $\leq 5.0 \times 10^5$ Da

HA of $\leq 5.0 \times 10^5$ Da was prepared from HA of $5.0-7.5 \times 10^5$ Da by digestion with hyaluronidase type IV-S derived from bovine testes (Sigma-Aldrich Canada, Oakville, Ontario, Canada) for 60 minutes at 37° C., by sonication on ice (Branson Sonifier Model 450, Danbury, Conn., USA) for 20 minutes at maximal intensity, or by autoclaving (Amsco-Steris International, Model 2002, Mentor, Ohio, USA) for 30 minutes.

The HA obtained was electrophoresed in 0.5% agarose gels prepared in TAE buffer (40 mM Tris, 20 mM acetic acid and 2.0 mM EDTA, pH 7.9) for 3 hours at 100 V (Lee et al. Anal. Biochem. 219:278, 1994). The molecular mass distribution of the HA was visualized using 0.005% of the cationic dye Stains-All (1-Ethyl-2-[3-(1-ethylnapthol[1,2-d] thiazolin-2-ylidene)-2-methylpropenyl]napthol[1,2-d]thiazolium Bromide; Sigma-Aldrich, Oakville, Ontario, Canada) and the gel photo was scanned using 1D software (Advance American Biotechnology, Fullerton, Calif., USA). The molecular mass of HA was <1.5×10$^4$ Da after hyaluronidase, about 1.0–3.0×10$^5$ Da after sonication, and about 3.0–5.0×10$^5$ Da after autoclaving.

EXAMPLE 4

Measurement of Cell Proliferation

Cell proliferation was measured using dimethylthiazoldiphenyltetrazolium (MTT) reduction (Mosman et al. J. Immunol. Methods 65:55, 1983). Unless otherwise stated, 100 µl of 5 mg of MTT (Sigma-Aldrich, St. Louis, Mo., USA) dissolved in 1 ml of PBS was added into each well. After 4 h, medium was removed from each well, 1.0 ml of acid-isopropanol (0.04 N HCl in isopropanol) was added and reduced MTT was solubilized by mixing. Absorbency of the reaction product was measured at a wavelength of 570 nm using a multiplate spectrophotometer reader (Elx800 Model, Bio-TEK Instruments Inc., Winooski, Vt., USA).

EXAMPLE 5

Inhibition of Cell Proliferation with HA

Unless stated otherwise 1.0×10$^5$ cells/ml were seeded in 6-well flat-bottom tissue culture plates and were maintained for 48 h at 37° C. in a 5% CO$_2$ atmosphere.

PC-3, LNCAP and Du-145 human prostate cancer cells; MCF-7 human breast cancer cells; HT-1080 human fibrosarcoma cancer cells; B16F1 murine melanoma cells; and, UMUC-3, RT-4, HT-1376 and T-24 human bladder cancer cells were incubated with 0.8, 8.0 and 80 µg/ml of 5.0–7.5×10$^5$ Da HA (Table 2).

TABLE 2

Inhibition of cell proliferation with 0.5–7.5 × 10$^5$ Da HA

| | % INHIBITION | | |
| --- | --- | --- | --- |
| CELLS | 0.8 µg/ml | 8.0 µg/ml | 80.0 µg/ml |
| PC-3 | 15 | 26 | 30 |
| LNCaP | 7 | 13 | 26 |
| Du-145 | 6 | 15 | 38 |
| MCF-7 | 19 | 24 | 35 |
| HT-1080 | 4 | 4 | 36 |
| B16F1 | 20 | 20 | 30 |
| UMUC-3 | 10 | 10 | 2 |
| RT-4 | 12 | 13 | 5 |
| HT-1376 | 0 | 3 | 1 |
| T-24 | 10 | 8 | 0 |

As shown in Table 2, inhibition of proliferation of PC-3, LNCaP, Du-14, MCF-7, HT-1080 and B16F1 cancer cells increased with increasing concentrations of HA, whereas inhibition of proliferation of UMUC-3, RT-4, HT-1376 and T-24 cancer cells did not increase with increasing concentrations of HA.

PC-3. LNCaP and Du-145 human prostate cancer cells were incubated with 8.0 µg/ml of 5.0–7.5×10$^5$ Da HA or of <1.5×10$^4$ Da HA (Table 3).

TABLE 3

Inhibition of cell proliferation

| | % INHIBITION | |
| --- | --- | --- |
| CELLS | 5.0–7.5 × 10$^5$ Da HA 8.0 µg/ml | <1.5 × 10$^4$ Da HA 8.0 µg/ml |
| PC-3 | 26 | 5 |
| LNCaP | 13 | 24 |
| Du-145 | 15 | 37 |

PC-3 cancer cell proliferation was inhibited more by 5.0–7.5×10$^5$ Da HA, whereas LNCaP and Du-145 cancer cell proliferation was inhibited more by <1.5×10$^4$ Da HA.

EXAMPLE 6

HA Potentiation of the Anti-neoplastic Effect of M-DNA and MCC

Unless stated otherwise 2.0×10$^4$ cells/ml were seeded in 24-well plates and were maintained for 48 h at 37° C. in a 5% CO$_2$ atmosphere. MTT was used at 50 µl per well.

T-24 human bladder cancer cells, PC-3 and Du-145 human prostate cancer cells, and MCF-7 human breast cancer cell were incubated with saline or with 80.0 µg/ml of 5.0–7.5×10$^5$ Da HA+1.0 µg/ml of M-DNA (Table 4).

TABLE 4

HA potentiation of M-DNA inhibition of cell proliferation

| | % INHIBITION 5.0–7.5 × 10$^5$ Da HA | |
| --- | --- | --- |
| CELLS | Saline | 80.0 µg/ml |
| T-24 + saline | 0 | 0 |
| T-24 + M-DNA | 28 | 36 |
| PC-3 + saline | 0 | 30 |
| PC-3 + M-DNA | 10 | 50 |
| Du-145 + saline | 0 | 38 |
| Du-145 + M-DNA | 11 | 58 |
| MCF-7 + saline | 0 | 35 |
| MCF-7 + M-DNA | 13 | 52 |

As shown in Table 4, HA potentiated the anti-neoplastic effect of M-DNA on T-24, PC-3, Du-145 and MCF-7 cancer cells.

HT-1376, RT-4 and T-24 human bladder cancer cells were incubated with 0.8 µg/ml of 5.0–7.5×10$^5$ Da HA+1.0 µg/ml of MCC (Table 5).

TABLE 5

HA potentiation of MCC inhibition of cell proliferation

| | % INHIBITION | |
| --- | --- | --- |
| CELLS | Saline | 5.0–7.5 × 10$^5$ Da HA at 0.8 µg/ml |
| HT-1376 + saline | 0 | 3 |
| HT-1376 + MCC | 21 | 34 |
| RT-4 + saline | 0 | 13 |
| RT-4 + MCC | 16 | 37 |
| T-24 + saline | 0 | 8 |
| T-24 + MCC | 31 | 45 |

As shown in Table 5, HA potentiated the anti-neoplastic effect of MCC on H-1376, RT-4 and T-24 cancer cells.

EXAMPLE 7

HA Potentiation of the Anti-neoplastic Effect of Synthetic Oligonucleotides

MCF-7 human breast cancer cells ($2.5 \times 10^5$ cells/ml) were incubated as in Example 6 with 0.0, 0.01 and 0.1 µg/ml of $5.0–7.5 \times 10^5$ Da HA+100 µg/ml of the synthetic 6 base oligonucleotide $GG(GT)_1GG$ (SEQ ID NO:1) or +100 µg/ml of the 15 synthetic 27 base oligonucleotide $(GT)_{13}G$ (SEQ ID NO:2) (Table 6). MTT was used at 50 µl per well.

TABLE 6

HA potentiation of inhibition of synthetic oligonucleotide inhibition of cell proliferation

| SEQUENCES | % INHIBITION $5.0–7.5 \times 10^5$ Da HA | | |
|---|---|---|---|
| 100 µg/ml | 0.0 µg/ml | 0.01 µg/ml | 0.1 µg/ml |
|  | 0 | 6 | 5 |
| $GG(GT)_1GG$-(6 bases) - SEQ ID NO: 1 | 20 | 34 | 33 |
| $(G_1T)_{13}G$-(27 bases) - SEQ ID NO: 2 | 44 | 51 | 59 |

As shown in Table 6, 0.01 µg/ml HA and 0.1 µg/ml HA potentiated the anti-neoplastic activity of 6 base $GG(GT)_1GG$ (SEQ ID NO:1) and 0.01 µg/ml HA potentiated the antineoplastic activity of 27 base $(G_1T)_{13}G$ (SEQ ID NO:2).

EXAMPLE 8

HA Potentiation of the Anti-neoplastic Effect of Chemotherapeutic Drugs

RT-4 human bladder cancer cells and MCF-7 human breast cancer cells were incubated as in Example 6 with 0.0, 0.008 or 0.08 µg/ml of $5.0–7.5 \times 10^5$ Da HA+0.1 µg/ml of CIS, +1.0 µg/ml of 5-FU or +10 µg/ml of 5-FU (Table 7).

TABLE 7

HA potentiation of chemotherapeutic drug inhibition of cell proliferation

| CELLS | % INHIBITION $5.0–7.5 \times 10^5$ Da HA | | |
|---|---|---|---|
|  | Saline | 0.008 µg/ml | 0.08 µg/ml |
| RT-4 + saline | 0 | 0 | 0 |
| RT-4 + CIS at 0.1 µg/ml | 2 | 13 | 15 |
| RT-4 + 5-FU at 1.0 µg/ml | 14 | 18 | 19 |
| MCF-7 + saline | 0 | 12 | 12 |
| MCF-7 + 5-FU at 10 µg/ml | 18 | 32 | 31 |

As shown in Table 7, 0.008 µg/ml and 0.08 µg/ml HA potentiated the anti-neoplastic effect of 0.1 µg/ml CIS and of 1.0 µg/ml 5-FU on RT-4 cancer cells and the anti-neoplastic effect of 10 µg/ml of 5-FU on MCF-7 cancer cells.

EXAMPLE 9

CD44 Cell Surface Receptors and HA Inhibition of Proliferation

CD44 is a cell surface HA receptor that has multiple variants (Screaton et al.

Proc. Natl. Acad. Sci. USA, 89:12160, 1992). CD44 variants are selectively expressed in human tumors and are over-expressed on numerous tumor cell lines (Naot et al. Adv. Cancer Res. 71:241, 1997). It has been suggested that CD44 receptors on cancer cells enables HA to deliver effective amounts of the highly lipophilic chemotherapeutic drug paclitaxel (TAXOL®) into cancer cells at low paclitaxel dosage amounts because the paclitaxel binds to the HA that, in turn, binds to the CD44 receptors (PCT/CA98/00660).

To determine if HA binding to CD44 receptors correlates with inhibition of cell proliferation, CD44 receptor expression was detected by flow cytometry (FCM) using the fluorescent anti-HA receptor monoclonal antibody FITC-CD44 (clone G44-26 (C26), Pharmingen, Mississauga, Ontario, Canada). Briefly, cells were pelleted by centrifugation at 180×G for 5 min at RT, washed twice in PBS and incubated with FITC-CD44 at the concentration recommended by the manufacturer for 20 min at 4° C in the dark. The cells were then washed twice in PBS by centrifugation and cell fluorescence was measured at 488 nm excitation and 530 nm emission (FL1 detector).

Data were analyzed on a FACSCALIBUR using the program CELLQUEST (Becton Dickinson, San Jose, Calif., USA).

CD44 expression and the inhibition of proliferation by $5.0–7.5 \times 10^5$ Da HA were measured using Jurkat T cell leukemia cells; MCF-7 human breast cancer cells; RT-4, T-24, HT-1376 and UMUC-3 human bladder cancer cells; and, PC-3, Du-145 and LNCaP prostate cancer cells (Table 8)

TABLE 8

CD44 cell surface expression and HA inhibition of cell proliferation

| CELLS | CD44 expression in mean fluorescent units | | $5.0–7.5 \times 10^5$ Da HA - 80 µg/ml |
|---|---|---|---|
|  | Unstained cells | Cells + anti-CD44 | % inhibition of proliferation |
| HT-1376 | 4 | 200 | 1 |
| RT-4 | 4 | 60 | 5 |
| T-24 | 3 | 1800 | 0 |
| UMUC-3 | 3 | 1800 | 2 |
| PC-3 | 6 | 400 | 30 |
| Du-145 | 3 | 450 | 38 |
| MCF-7 | 3 | 70 | 35 |
| Jurkat T | 3 | 3 | 0 |
| LNCaP | 6 | 6 | 26 |

As shown in Table 8, expression of CD44 receptors by cancer cells did not correlate with inhibition of proliferation by HA. PC-3 cancer cells express CD44 receptors, whereas LNCaP cancer cells do not express CD44 receptors (Lokeshwar et al.

Anticancer Res. 15:1191, 1995). However, as shown in Table 8, HA inhibition of proliferation of PC-3 cancer cells (30%) and of LNCaP cancer cells (26%) was not significantly different.

EXAMPLE 10

Induction of Cytokine Production

Peripheral blood mononuclear cells (hereinafter, "PBMCs") were isolated from the blood of 5 healthy humans by Ficoll-Hypaque (Amersham Pharmacia Biotech, Baie d'Urfée, Québec, Canada) density gradient centrifugation of whole blood. Stimulation of IL-6 and IL-12 production by the immune system cells was determined using the appropriate commercial ELISA (BioSource, Camarillo, Calif., USA). Results are expressed as the "fold" (x) increases in cytokine production by treated cells compared to control cells.

PBMCs were incubated with 1 mg/ml of $5.0–7.5 \times 10^5$ Da and production of IL-6 and IL-12 was determined (Table 9).

TABLE 9

| | Cytokine production | |
|---|---|---|
| Individual | IL-6 | IL-12 |
| 1 | 3.8x | 25.2x |
| 2 | 1.8x | 7.1x |
| 3 | 4.1x | 26.5x |
| 4 | 1.4x | 10.0x |
| 5 | 6.3x | 8.5x |

As shown in the Table 9, HA stimulated both IL-6 and IL-12 production by immune system cells.

PBMCs, isolated from the blood of individual #1, were incubated with 0.008, 0.04, 0.2 and 1 mg/ml of $5.0–7.5 \times 10^5$ Da (Table 10)

TABLE 10

| | Cytokine production | |
|---|---|---|
| $5.0–7.5 \times 10^5$ Da HA (mg/ml) | IL-6 | IL-12 |
| 0.008 | 2.4x | 4.9x |
| 0.040 | 3.5x | 13.8x |
| 0.200 | 2.9x | 8.5x |
| 1.000 | 3.8x | 25.2x |

As shown in the Table 10, HA at 0.008, 0.04, 0.2 and 1 mg/ml, stimulated both IL-6 and IL-12 production by immune system cells.

EXAMPLE 11

Effect of Saline, HA, M-DNA, MCC, HA+M-DNA and HA+MCC on PC3 Tumors in Mice

PC-3 human prostate cancer cells are implanted subcutaneously into 224 male nude BALB/c mice. The mice are divided into 28 groups of 8 mice (Table 11).

TABLE 11

Effect of saline, HA, M-DNA, MCC, HA + M-DNA and HA + MCC

| | Saline | M-DNA or MCC 0.02 mg/kg | M-DNA or MCC 0.2 mg/kg | M-DNA or MCC 2.0 mg/kg |
|---|---|---|---|---|
| Saline | Group 1 | Groups 5 and 17 | Groups 9 and 21 | Groups 13 and 25 |
| HA at 16.0 mg/kg | Group 2 | Groups 6 and 18 | Groups 10 and 22 | Groups 14 and 26 |
| HA at 1.6 mg/kg | Group 3 | Groups 7 and 19 | Groups 11 and 23 | Groups 15 and 27 |
| HA at 0.16 mg/kg | Group 4 | Groups 8 and 20 | Groups 12 and 24 | Groups 16 and 28 |

Saline, HA, M-DNA, MCC, HA+M-DNA and HA+MCC are administered intravenously on day 0 and at 3-day intervals for 4 weeks (10 injections) at which time the mice are sacrificed and tumor mass and number of metastases are determined. Groups 2 to 28 mice have less tumor mass and fewer metastases than Group 1 mice. Groups 6–8, 10–12, 14–16, 18–20, 22–24 and 26–28 have less tumor mass and fewer metastases than Groups 5, 9, 13, 17, 21 and 25 mice.

EXAMPLE 12

Effect of Saline, HA, M-DNA, MCC, HA+M-DNA and HA+MCC on LNCaP Tumors in Mice

LNCaP human prostate cancer cells (CD44 null) are implanted subcutaneously into 224 male nude BALB/c mice. The mice are divided into 28 groups of 8 mice (Table 12).

TABLE 12

Effect of saline, HA, M-DNA, MCC, HA + M-DNA and HA + MCC

| | Saline | M-DNA or MCC 0.02 mg/kg | M-DNA or MCC 0.2 mg/kg | M-DNA or MCC 2.0 mg/kg |
|---|---|---|---|---|
| Saline | Group 1 | Groups 5 and 17 | Groups 9 and 21 | Groups 13 and 25 |
| HA at 16.0 mg/kg | Group 2 | Groups 6 and 18 | Groups 10 and 22 | Groups 14 and 26 |
| HA at 1.6 mg/kg | Group 3 | Groups 7 and 19 | Groups 11 and 23 | Groups 15 and 27 |
| HA at 0.16 mg/kg | Group 4 | Groups 8 and 20 | Groups 12 and 24 | Groups 16 and 28 |

Saline, HA, M-DNA, MCC, HA+M-DNA and HA+MCC are administered intravenously on day 0 and at 3-day intervals for 4 weeks (10 injections) at which time the mice are sacrificed and tumor mass and number of metastases are determined. Groups 2 to 28 mice have less tumor mass and fewer metastases than Group I mice. Groups 6–8, 10–12, 14–16, 18–20, 22–24 and 26–28 have less tumor mass and fewer metastases than Groups 5, 9, 13, 17, 21 and 25 mice. These results show that treatment outcome does not depend on CD44 expression by the cancer cells.

EXAMPLE 13

Effect of Saline, HA, M-DNA, MCC, HA+M-DNA and HA+MCC on B16F1 Tumors in Mice

B16F1 cancer cells are implanted intravenously into 224 female C57BL/6 mice. The mice are divided into 28 groups of 8 mice (Table 13).

TABLE 13

Effect of saline, HA, M-DNA, MCC, HA + M-DNA
and HA + MCC on B16F1 tumors

|  | Saline | M-DNA or MCC 0.02 mg/kg | M-DNA or MCC 0.2 mg/kg | M-DNA or MCC 2.0 mg/kg |
|---|---|---|---|---|
| Saline | Group 1 | Groups 5 and 17 | Groups 9 and 21 | Groups 13 and 25 |
| HA at 16.0 mg/kg | Group 2 | Groups 6 and 18 | Groups 10 and 22 | Groups 14 and 26 |
| HA at 1.6 mg/kg | Group 3 | Groups 7 and 19 | Groups 11 and 23 | Groups 15 and 27 |
| HA at 0.16 mg/kg | Group 4 | Groups 8 and 20 | Groups 12 and 24 | Groups 16 and 28 |

Saline, HA, M-DNA, MCC, HA+M-DNA and HA+MCC are administered intratumorally in saline on day 0 and at 3 day intervals for 4 weeks (10 injections) at which time the mice are sacrificed and tumor mass and number of metastases are determined. Groups 2 to 28 mice have less tumor mass and fewer metastases than Group 1 mice. Groups 6–8, 10–12, 14–16, 18–20, 22–24 and 26–28 have less tumor mass and fewer metastases than Groups 5, 9, 13, 17, 21 and 25 mice.

EXAMPLE 14

Effect of Saline, HA, CIS, 5-FU, HA+CIS and HA+5-FU on PC3 Tumors in Mice

PC-3 cancer cells are implanted subcutaneously into 224 male nude BALB/c mice. The mice are divided into 28 groups of 8 mice (Table 14).

TABLE 14

Effect of saline, HA, CIS, 5-FU, HA + CIS
and HA + 5-FU on PC3 tumors

|  | Saline | CIS or 5-FU 0.1 mg/kg | CIS or 5-FU 1.0 mg/kg | CIS or 5-FU 10.0 mg/kg |
|---|---|---|---|---|
| Saline | Group 1 | Groups 5 and 17 | Groups 9 and 21 | Group 13 and 25 |
| HA at 16.0 mg/kg | Group 2 | Groups 6 and 18 | Groups 10 and 22 | Group 14 and 26 |
| HA at 1.6 mg/kg | Group 3 | Groups 7 and 19 | Groups 11 and 23 | Group 15 and 27 |
| HA at 0.16 mg/kg | Group 4 | Groups 8 and 20 | Groups 12 and 24 | Groups 16 and 28 |

Saline, HA, CIS, 5-FU, HA+CIS and HA+5FU are administered intravenously in saline on day 0 and at 3 day intervals for 4 weeks (10 injections) at which time the mice are sacrificed and tumor mass and number of metastases are determined. Groups 2 to 28 mice have less tumor mass and fewer metastases than Group 1 mice. Groups 6–8, 10–12, 14–16, 18–20, 22–24 and 26–28 have less tumor mass and fewer metastases than Groups 5, 9, 13, 17, 21 and 25 mice.

EXAMPLE 15

Effect of Saline, HA, CIS, 5-FU, HA+CIS and HA+5-FU on LNCaP Tumors in Mice

LNCaP cancer cells (CD44 null) are implanted subcutaneously into 224 male nude BALB/c mice. The mice are divided into 28 groups of 8 mice (Table15).

TABLE 15

Effect of saline, HA, CIS, 5-FU, HA + CIS
and HA + 5-FU on LNCaP tumors

|  | Saline | CIS or 5-FU 0.1 mg/kg | CIS or 5-FU 1.0 mg/kg | CIS or 5-FU 10.0 mg/kg |
|---|---|---|---|---|
| Saline | Group 1 | Groups 5 and 17 | Groups 9 and 21 | Group 13 and 25 |
| HA at 16.0 mg/kg | Group 2 | Groups 6 and 18 | Groups 10 and 22 | Group 14 and 26 |
| HA at 1.6 mg/kg | Group 3 | Groups 7 and 19 | Groups 11 and 23 | Group 15 and 27 |
| HA at 0.16 mg/kg | Group 4 | Groups 8 and 20 | Groups 12 and 24 | Groups 16 and 28 |

Saline, HA, CIS, 5-FU, HA+CIS and HA+5FU are administered intravenously in saline on day 0 and at 3 day intervals-for 4 weeks (10 injections) at which time the mice are sacrificed and tumor mass and number of metastasis are determined. Groups 2 to 28 mice have less tumor mass and fewer metastases than Group 1 mice. Groups 6–8, 10–12, 14–16, 18–20, 22–24 and 26–28 have less tumor mass and fewer metastases than Groups 5, 9, 13, 17, 21 and 25 mice. These results show that treatment outcome does not depend on CD44 expression by the cancer cells.

EXAMPLE 16

Effect of Saline, HA, CIS, 5-FU, HA+CIS and HA+5-FU on B16F1 Tumors in Mice

B16F1 cancer cells are implanted subcutaneously into 224 female C57BL/6 mice. The mice are divided into 28 groups of 8 mice (Table 16).

TABLE 16

Effect of saline, HA, CIS, 5-FU, HA + CIS
and HA + 5-FU on B16F1 tumors

|  | Saline | CIS 0.01 mg/kg or 5-FU 1.0 mg/kg | CIS 0.1 mg/kg or 5-FU 10.0 mg/kg | CIS 1.0 mg/kg or 5-FU 100.0 mg/kg |
|---|---|---|---|---|
| Saline | Group 1 | Groups 5 and 17 | Groups 9 and 21 | Group 13 and 25 |
| HA-N at 16.0 mg/kg | Group 2 | Groups 6 and 18 | Groups 10 and 22 | Group 14 and 26 |
| HA-N at 1.6 mg/kg | Group 3 | Groups 7 and 19 | Groups 11 and 23 | Group 15 and 27 |
| HA-N at 0.16 mg/kg | Group 4 | Groups 8 and 20 | Groups 12 and 24 | Groups 16 and 28 |

Saline, HA, CIS, 5-FU, HA+CIS and HA+5FU are administered intravenously in saline on day 0 and at 3 day intervals for 4 weeks (10 injections) at which time the mice are sacrificed and tumor mass and number of metastases are determined. Groups 2 to 28 mice have less tumor mass and fewer metastases than Group 1 mice.

While the invention has been described in detail and with reference to specific embodiments thereof, it will be apparent to one skilled in the art that various changes and modifications can be made therein without departing from the spirit and scope thereof.

We claim:

1. A composition comprising purified hyaluronic acid, a second anti-neoplastic agent and a pharmaceutically acceptable carrier, wherein the second anti-neoplastic agent is *Mycobacterium phlei* DNA (M-DNA), *Mycobacterium phlei* cell wall complex (MCC), an oligonucleotide, or a combination thereof, wherein the oligonucleotide is SEQ ID NO:1 or SEQ ID NO: 2.

2. A method comprising administering a composition comprising purified hyaluronic acid, a second anti-neoplastic agent and a pharmaceutically acceptable carrier to a mammal having cancer in an amount effective to treat the cancer,
  wherein the second anti-neoplastic agent is *Mycobacterium phlei* DNA (M-DNA), *Mycobacterium phlei* DNA (M-DNA)-*Mycobacterium phlei* cell wall complex (MCC), an oligonucleotide, tamoxifen, or a combination thereof, and wherein the oligonucleotide is SEQ ID NO: 1 or SEQ ID NO: 2.

3. A method comprising administering a composition comprising purified hyaluronic acid, a second anti-neoplastic agent and a pharmaceutically acceptable carrier to a mammal having cancer in an amount effective to treat the cancer,
  wherein the second anti-neoplastic agent is a *Mycobacterium phlei* DNA (M-DNA), *Mycobacterium phlei* DNA (M-DNA)-*Mycobacterium phlei* cell wall complex (MCC), an oligonucleotide or tamoxifen,
  wherein the oligonucleotide is SEQ ID NO: 1 or SEQ ID NO: 2, and,
  the cancer is squamous cell carcinoma, fibrosarcoma, sarcoid carcinoma, melanoma, mammary cancer, lung cancer, colorectal cancer, renal cancer, osteosarcoma, cutaneous melanoma, basal cell carcinoma, pancreatic cancer, bladder cancer, brain cancer, ovarian cancer, prostate cancer, leukemia or lymphoma.

4. The composition of claim 1, wherein the purified hyaluronic acid is hyaluronan, hyaluronate, a salt of hyaluronic acid, a homologue, an analogue, a derivative, a complex, ester, fragment or subunit of hyaluronic acid that is suitable for use in a mammal.

5. The composition of claim 1, wherein the pharmaceutically acceptable carrier is a liquid carrier, a solid carrier or a combination thereof.

6. The composition of claim 5, wherein the liquid carrier is water, saline, a physiologically acceptable buffer, an aqueous suspension, an oil emulsion, a water-in-oil emulsion, a water-in-oil-in-water emulsion, a site-specific emulsion, a long residence emulsion, a sticky emulsion, a microemulsion, a nanoemulsion, a mineral oil, neutral oil or mixture thereof.

7. The composition of claim 5, wherein the solid carrier is a chemical carrier, a biological carrier, a particle, a microparticle, a nanoparticle, a microsphere, a nanosphere, a minipump, a bacterial cell wall extract, a biodegradable or non-biodegradable natural or synthetic polymer that allow for sustained release of the composition, or a mixture thereof.

8. The method of claim 2, wherein the cancer is squamous cell carcinoma, fibrosarcoma, sarcoid carcinoma, melanoma, mammary cancer, lung cancer, colorectal cancer, renal cancer, osteosarcoma, cutaneous melanoma, basal cell carcinoma, pancreatic cancer, bladder cancer, brain cancer, ovarian cancer, prostate cancer, leukemia or lymphoma.

9. The method of claim 2, wherein the administering is oral, topical, subcutaneous, transdermal, subdermal, intramuscular, intra-peritoneal, intra-vesical, intra-articular, intra-arterial, intra-venous, intra-dermal, intra-cranial, intra-lesional, intra-tumoral, intra-ocular, intra-pulmonary, intra-spinal, nasal inhalation, pulmonary inhalation, impression into skin, electroporation, through an osmotic minipump, or through a cannula to the site of interest.

10. A method comprising administering a composition comprising purified hyaluronic acid, a second anti-neoplastic agent and a pharmaceutically acceptable carrier to a mammal having cancer in an amount effective to treat the cancer,
  wherein die second anti-neoplastic agent is *Mycobacterium phlei* DNA (M-DNA), *Mycobacterium phlei* DNA (M-DNA)-*Mycobacterium phlei* cell wall complex (MCC), or an oligonucleotide, or a combination thereof, wherein the oligonucleotide is SEQ ID NO: 1 or SEQ ID NO: 2.

11. The method of claim 10, wherein the cancer is squamous cell carcinoma, fibrosarcoma, sarcoid carcinoma, melanoma, mammary cancer, lung cancer, colorectal cancer, renal cancer, osteosarcoma, cutaneous melanoma, basal cell carcinoma, pancreatic cancer, bladder cancer, brain cancer, ovarian cancer, prostate cancer, leukemia or lymphoma.

12. The method of claim 10, wherein the administering is oral, topical, subcutaneous, transdermal, subdermal, intra-muscular, intra-peritoneal, intra-vesical, intra-articular, intra-arterial, intra-venous, intra-dermal, intra-cranial, intra-lesional, intra-tumoral, intra-ocular, intra-pulmonary, intra-spinal, nasal inhalation, pulmonary inhalation, impression into skin, electroporation, through an osmotic minipump, or though a cannula to the site of interest.

13. The composition of claim 1, wherein the purified hyaluronic acid has a molecular mass of between about $1\times10^3$ and $1\times10^7$ Daltons.

14. The composition of claim 1, wherein the purified hyaluronic acid has a molecular mass of between about $5\times10^4$ and $1\times10^6$ Daltons.

15. The composition of claim 1, wherein the purified hyaluronic acid has a molecular mass of between about $1\times10^4$ and $8\times10^5$ Daltons.

16. The method of claim 2, wherein the amount of purified hyaluronic acid administered per dose is about 0.001 to about 25 mg per kg body weight.

17. The method of claim 2, wherein the amount of purified hyaluronic acid administered per dose is about 0.01 to about 10 mg per kg body weight.

18. The method of claim 10, wherein the amount of purified hyaluronic acid administered per dose is about 0.001 to about 25 mg per kg body weight.

19. The method of claim 10, wherein the amount of purified hyaluronic acid administered per dose is about 0.01 to about 10 mg per kg body weight.

* * * * *